United States Patent [19]
Babaï et al.

[11] Patent Number: 5,539,096
[45] Date of Patent: Jul. 23, 1996

[54] GENES DIFFERENTIALLY EXPRESSED IN METASTATIC AND NON-METASTATIC RAT RHABDOMYOSARCOMA CELL LINES

[75] Inventors: Féridoun Babaï, Outremont; Luc Daigneault, Montréal; AndréRoyal, Brossard, all of Canada

[73] Assignee: Université de Montréal, Montreal, Canada

[21] Appl. No.: 302,537

[22] Filed: Sep. 8, 1994

[51] Int. Cl.$^6$ .......................... C07H 21/02; C07H 21/04
[52] U.S. Cl. ...................... 536/24.3; 536/24.31
[58] Field of Search .................. 435/6; 935/77, 935/78; 536/24.3, 24.31

[56] References Cited

PUBLICATIONS

Babal F., *J. Ultrastructure Res.*, 1976, 56:287–303.
Frixen U. H. et al., *Journal of Cell Biology*, 1991, 113(1):173–85.
Phillips SM et al., *Journal of the National Cancer Institute*, 1990, 82(3):199–203.
Ebralidze A et al., *Genes & Development*, 1989, 3(7):1086–93.
Murakami A et al., *Cell Growth & Differentiation*, 1990, 1(5):225–31.
Günthert U et al., *Cell*, 1991, 65:13.
Schalken JA et al., *Cancer Res.*, 1988, 48:2042–2046.
Wallet V et al., *Journal of the National Cancer Institute*, 1990, 82(14):1199–202.
Dear TN et al., *Cancer Research*, 1990, 50(5):1667.
Elvin P et al., *Br. J. Cancer*, 1988, 57:36–42.
Liotta LA, *Amer. J. Pathol.*, 1984, 117:339–348.
Sharp MGF et al., *Br. J. Cancer*, 1990, 61:83–88.
Basset P et al., *Nature*, 1990, 348:699–704.
Adams SM et al., *Human molecular genetics*, 1992, 1(2):91–96.
Adams SM et al., *Br. J. Cancer*, 1992, 65:65–71.
Armstrong PB, *Invasiveness of non–malignant cells*. In: Invastion. Experimental and clinical implications. Mareal MM and Calman, KC, ed. Oxford University Press. Oxford, 1984.
Babaï F, and Royal A, *Rat myoblastic sarcoma cell lines: A model for the study of invasion, metastatis and myogenic differentiation*. Lab. Investigation, 1994, 70:907–915.
Sambrook J, Fritsch EF, and Maniatis T. *Molecular cloning: A laboratory manual*, second edition, Cold Spring Harbor Laboratory Press, 1989.
Croze F et al., *Endocrinology*, 1990, 127:2665–2672.
Mauxion F et al., *Nucleic Acids Res.*, 1987, 15:7638.
Matrisian LM et al., *Nucleic Acids Res*, 1985, 13:711–726.
Grenett HE et al., *Gene*, 1992, 110:239–243.
Kuwano Y et al., *Biochem. Biophys. Res. Commun.*, 1991, 175:551–555.
Devi KR et al., *Biochem. Biophys. Acta*, 1989, 1008:258–262.
Wool IG et al., *Biochimie*, 1991, 73:861–870.
Michaelson J, *Immunogenetics*, 1983, 17:219.
Ljunggren H–G et al., *J. Immunol.*, 1990, 145:380–386.
Argiles JM et al., *Medical Hypotheses*, 1990, 32(2):151–155.
Hart IR et al., *Biochimica Et Biophysica Acta*, 1989, 989(1):65–84.
Steeg PS et al., *J. Natl. Cancer Inst.*, 1988, 80:200–204.
Dear TN et al., *Cancer Res.*, 1989, 49:5323–5328.
Kondoh et al., *Cancer Res.*, 1992, 52:791–796.
Pogue–Geile et al., *Mol. and Cell. Biol.*, 1991, 11:3842–3849.
Rabbitts, T. H. et al., *Nature Genetics*, 1993, 4:175–180.

*Primary Examiner*—W. Gary Jones
*Assistant Examiner*—Eggerton Campbell
*Attorney, Agent, or Firm*—Klauber & Jackson

[57] ABSTRACT

The present invention relates to polynucleotide sequences and proteins that are differentially expressed in invasive or metastasis cancer cells during malignant tumor progression of cancer, for example in rhabdomyosarcoma and which may thus serve as general molecular markers in metastatic disease as well as providing a basis for therapy. The present invention also relates to a method of diagnosis of malignant diseases based on the detection of such markers.

2 Claims, 12 Drawing Sheets

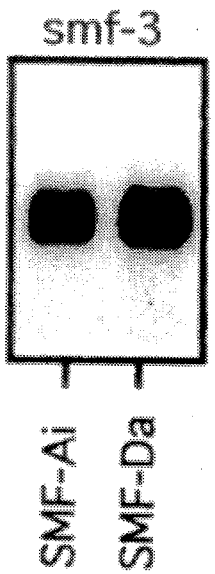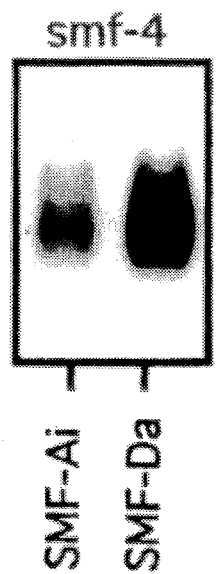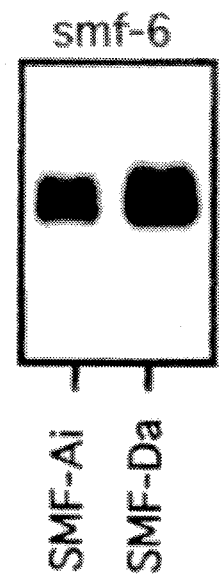
Fig. 4A  Fig. 4B  Fig. 4C
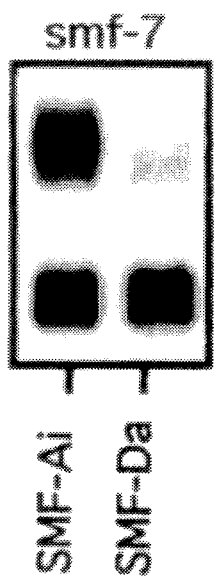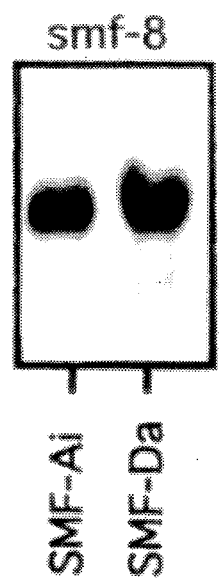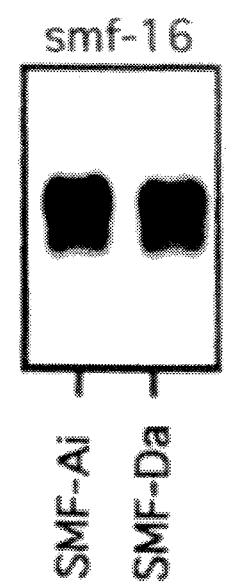
Fig. 4D  Fig. 4E  Fig. 4F

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
      ( A ) LENGTH: 174 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:1:

```
CTATCATTTA  TCCACAAGAT  AGATAGCAAT  GAGCACACCA  TCTCCTCATA  TCTTACCCTA        60

AATATTTATG  CATGTTTAAA  AAATTGGAGA  CTAATATCCT  AGATTTCCGG  AATAATAAAG       120

CTTCAATGAG  TGGTTTTGAT  CAGAATAATA  AATATGGTTA  AGAACAAGAA  AAAA             174
```

( 2 ) INFORMATION FOR SEQ ID NO:2:

( i ) SEQUENCE CHARACTERISTICS:
      ( A ) LENGTH: 149 base pairs (B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:2:

| GGCCGCTGCA | TACGAAGTGA | TCAAGCTGAA | GGTTACACAT | CCTGGGCCAT | TGGCTCTCCG | 60 |
| TGGCAGACTT | GGCCGAGAGC | ATAATGAAGA | ACTAGGCGGG | TCGATCCATT | TCCGACATGA | 120 |
| TTAGGTCTCT | ATGGATCAAG | GAGGATCTG | | | | 149 |

(2) INFORMATION FOR SEQ ID NO:3:

(i) SEQUENCE CHARACTERISTICS:
(A) LENGTH: 154 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:3:

| TTTGGTGTTT | TTCCTTGGCA | TGACACTTGA | GTGGTTGGTT | CCATACATCC | ATATGCAGAT | 60 |
| CTTACATTCA | CGTGAATATT | GCAATGTCCA | CTACAGACCA | CATATAATAC | AGAAATATCT | 120 |
| GTAGAACATT | ATGCACAGAT | ATGCACGATG | GACT | | | 154 |

(2) INFORMATION FOR SEQ ID NO:4:

(i) SEQUENCE CHARACTERISTICS:
(A) LENGTH: 161 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:4:

| AGGATCACAG | TTTGTGAAAG | GATTTGGTGG | AATTGGAGGT | ATCTTGCGGT | ACGAGTAGAT | 60 |
| TCAGGAATGG | AATACCAAGG | AGGAGATGAC | GATTTTTGAC | CTTGATGACT | ACTAGGTAGT | 120 |
| CGACATGGTC | CGCAAACGGC | TCTCAGCATC | ACCAGGAGCA | T | | 161 |

(2) INFORMATION FOR SEQ ID NO:5:

(i) SEQUENCE CHARACTERISTICS:
(A) LENGTH: 136 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:5:

| TTTTTTAACG | GTTCCAACAT | TTCACCACAT | ATATTTCTGT | GCAGTCTAGC | CGAGAACGCC | 60 |
| ATGTAAATGG | GTCACTGCGA | GGCAGCGAAC | GCAGCAATTT | AGTTACTCTC | GATCAAGGGA | 120 |
| GAAACAACAG | TATGAC | | | | | 136 |

(2) INFORMATION FOR SEQ ID NO:6:

(i) SEQUENCE CHARACTERISTICS:
(A) LENGTH: 126 base pairs
(B) TYPE: nucleic acid
(C) STRANDEDNESS: single
(D) TOPOLOGY: linear 5,539,096

19

-continued

20

( i i ) MOLECULE TYPE: DNA (genomic)

( x i ) SEQUENCE DESCRIPTION: SEQ ID NO:6:

| CCGTCTGCCA | TGCCTCGGAA | AATTGAGGAA | TCAAGGACTT | TCTACTCACA | GCGCCGGCGG | 60 |
| AAGGATGCAA | ATCTGTCAAG | ATCAGAAAAA | ACAGGATAAT | GTAGTTCAAG | GTCGTGTAGC | 120 |
| AGGTAC | | | | | | 126 |

( 2 ) INFORMATION FOR SEQ ID NO:7:

( i ) SEQUENCE CHARACTERISTICS:
        ( A ) LENGTH: 102 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

| TGTTTTGATT | TCATCATGCT | GTTTAATCTA | GCATGTGCTT | AGAAGGCTTG | TTGGGCAGAG | 60 |
| TACAATATCT | CCAGCAGTTC | TAGAGACCAT | TCACCACTGC | GA | | 102 |

( 2 ) INFORMATION FOR SEQ ID NO:8:

( i ) SEQUENCE CHARACTERISTICS:
        ( A ) LENGTH: 156 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

| CACAGTCAGC | TCTTTATTGG | ACATGTTAAC | AAAAGCAGTT | TAGTCAAAAA | GACCAAAGCC | 60 |
| CATGTCATCC | TCGGATTCTT | CAGATTCTTC | CTTCTTTGCT | TCTACTTCTT | CTCCTCAGCT | 120 |
| GGGGCAGCGG | CGGCAGATGG | AGCAGGACAC | AGCAGG | | | 156 |

( 2 ) INFORMATION FOR SEQ ID NO:9:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

| AGCCTGGCAA | GATGGACTCA | GGGTGAGCAC | AGACAGGATC | GCAGGGAGAG | GCATATAGCT | 60 |
| GACTCTGAGT | TCTGACAGCT | CTCTGTACCA | GTGTACCTGT | ATTGTACTAC | ATCGATG | 117 |

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AGCAAGTTCA GCCTGGTTAA G         21

( 2 ) INFORMATION FOR SEQ ID NO:11:

( i ) SEQUENCE CHARACTERISTICS:
     ( A ) LENGTH: 24 base pairs
     ( B ) TYPE: nucleic acid
     ( C ) STRANDEDNESS: single
     ( D ) TOPOLOGY: linear ( i i ) MOLECULE TYPE: DNA (genomic)

( x i ) SEQUENCE DESCRIPTION: SEQ ID NO:11:

CTTATGAGTA TTTCTTCCAG GGTA 24

GENES DIFFERENTIALLY EXPRESSED IN METASTATIC AND NON-METASTATIC RAT RHABDOMYOSARCOMA CELL LINES

BACKGROUND OF THE INVENTION (a) Field of the Invention

The invention relates to genes which are involved in metastasis and their uses.

(b) Description of Prior Art

Metastasis involves the dissemination of tumor cells by invasion from the primary tumor site and proliferation of these cells at distant site in the target organ. The tumoral invasion and the metastasis are a multistep process (Babaï F., *J. Ultrastructure Res.*, 1976, 56:287–303; Liotta LA, *Amer. J. Pathol.*, 1984, 117:339–348) which requires several factors such as the liberation of the lyric enzymes in the invaded zone, a change in the motility and cellular adhesion of the tumor cell, intercellular communication and growth autonomy (Hart IR et al., *Biochimica Et Biophysica Acta*, 1989, 989(1):65–84).

A number of genes have been found to be associated with changes in metastatic potential. They fall into two categories: genes or gene products which are down regulated in metastatic cells and those which are up-regulated in metastatic cells. The first category includes nm23 (Steeg PS et al., *J. Natl. Cancer Inst.*, 1988, 80:200–204), WDNM1, WDNM2 (Dear TN et al., *Cancer Res.*, 1989, 49:5323–5328), and E-cadherin (Frixen UH et al., *Journal of Cell Biology*, 1991, 113(1):173–85). The other category includes pGM21 (Phillips SM et al., *Journal of the National Cancer Institute*, 1990, 82(3):199–203), Mts-1 (Ebralidze A et al., *Genes & Development*, 1989, 3(7):1086–93), hst (Murakami A et al., *Cell Growth & Differentiation*, 1990, 1(5):225–31), and CD44 (Günthert U et al., *Cell*, 1991, 65:13). However, the gene involved in each step of the invasion and the metastasis of all types of cancer and particularly of the rhabdomyosarcoma are not all well known.

To identify such genes, differential screening of the cDNA libraries has been used successfully by several groups using malignant and non-malignant tumors or tumor cell lines that retain a certain metastatic potential, either high or low. For example, fibronectin was isolated from a anaplastic non-metastazing subline AT-1 derived from a Dunning R-3327 rat prostatic tumor cell line. Fibronectin mRNA was down-modulated in metastatic variants of rat prostate tumor cell lines (Schalken JA et al., *Cancer Res.*, 1988, 48:2042–2046). Nm23 has been isolated from K-1735 murine melanoma cell lines with varying metastatic potential and higher expression of nm23 was associated with low metastatic potential (Steeg PS et al., *J. Natl. Cancer Inst.*, 1988, 80:200–204). The nm23 protein demonstrate a high homology with the nucleoside diphosphate kinase from Dictyostelium (Wallet V et al., *Journal of the National Cancer Institute*, 1990, 82(14):1199–20). WDNM1 and WDNM2 have been isolated from the rat mammary adenocarcinoma cell line DMBA-8 and are overexpressed in cell lines with lower metastatic potential (Dear TN et al., *Cancer Res.*, 1989, 49:5323–5328). The full length cDNA sequence of the WDNM2 gene exhibited complete homology to the rat NAD(P)H:menadione oxidoreductase cDNA sequence(Dear TN et al., *Cancer Research*, 1990, 50(5):1667). Elvin et al. (Elvin P et al., *Br. J. Cancer*, 1988, 57:36–42) have isolated a cDNA clone corresponding to the acidic ribosomal phosphoprotein P2 which is overexpressed in colorectal carcinomas of a human liver metastases than in primary colorectal tumors and normal tissue. However, Sharp et al. (*Br. J. Cancer*, 1990, 61:83–88) observed that the expression of the P2 gene is higher in human breast fibroadenomas than in carcinomas of the same tissue. Using the phenolemulsion reassociation technique with two cell sublines obtained from spontaneous mouse mammary carcinoma, the cDNA mts-1 has been isolated (Ebralidze A et al., *Genes & Development*, 1989, 3(7):1086–93). This cDNA is homologous to the mouse $Ca^{2+}$ binding protein and is overexpressed in cell lines with higher metastatic potential. Phillips et al. (Phillips SM et al., *Journal of the National Cancer Institute*, 1990, 82(3):199–203) have isolated by differential screening of a subtractive cDNA library constructed from a poorly metastatic rat mammary adenocarcinoma cell line (DMBA-8) and a highly metastatic variant line (DMBA-8 ascites), the clone pGM21 which is associated with high metastatic potential. Stromelysin 3 has been isolated from a human breast carcinomas and its expression is specific for stromal cells surrounding invasive but not non-invasive breast lesions (Basset Pet al., *Nature*, 1990, 348:699–704). Human breast carcinomas cDNA library was differentially screened with probes derived from both malignant (carcinoma) and non-malignant (fibroadenoma) tumors (Adams SM et al., *Br. J. Cancer*, 1992, 65:65–71). They have identified genes encoding for the elongation factor $-1\alpha$, human ubiquitin carboxyl-extension (Adams SM et al., *Human molecular genetics*, 1992, 1(2):91–96), clone bbcl (Adams SM et al., *Br. J. Cancer*, 1992, 65:65–71) and mitochondrial genes encoding subunit 2 cytochrome c oxydase, subunits 2 and 4 of NADH dehydrogenase and subunit 6 of $F_0F_1$ATPase (Sharp MGF et al., *Journal of pathology*, 1992, 168:163–168). Elongation factor $-1\alpha$, ubiquitin carboxyl-extension and bbcl are overexpressed in fibroadenomas than in carcinomas. Conversely, only the subunit 2 cytochrome c oxydase is overexpressed in carcinoma compared to fibroadenoma.

It would be highly desirable to be provided with the identification of genes implicated in the metastatis.

SUMMARY OF THE INVENTION

One aim of the present invention is to be provided with the identification of genes related or implicated in the metastasis.

The present invention is based at least in part on the discovery of nucleotide sequences and proteins that are differentially expressed in invasive or metastasis cancer cells during malignant tumor progression of cancer )for example in rhabdomyosarcoma) and which may thus serve as general molecular markers in metastatic disease as well as providing a basis for therapy. The present invention also relates to a method of diagnosis of malignant diseases based on the detection of such markers.

Thus, in accordance with one embodiment of the present invention there is provided a polynucleotide sequence which is differentially expressed in invasive or metastasis cancer cells during malignant tumor progression of cancer and fragments thereof. Such polynucleotide sequences includes genomic DNA sequences, corresponding RNA sequences, cDNA sequences derived from said RNA sequences, for example using reverse transcriptase, and any fragments of such sequences.

The polynucleotide sequences of the present invention are preferably characterized in that the cDNA sequences corresponding thereto contain the following sequence:

CTATCATTTA TCCACAAGAT AGATAGCAAT GAGCACACCA TCTCCTCATA TCTTACCCTA
60

AATATTTATG CATGTTTAAA AAATTGGAGA CTAATATCCT AGATTTCCGG AATAATAAAG
120

CTTCAATGAG TGGTTTTGAT CAGAATAATA AATATGGTTA AGAACAAGAA AAAA
174

(SEQ ID NO:1, designated smf-4);

GGCCGCTGCA TACGAAGTGA TCAAGCTGAA GGTTACACAT CCTGGGCCAT TGGCTCTCCG
60

TGGCAGACTT GGCCGAGAGC ATAATGAAGA ACTAGGCGGG TCGATCCATT TCCGACATGA
120

TTAGGTCTCT ATGGATCAAG GAGGATCTG
149

(SEQ ID NO:2);

TTTGGTGTTT TTCCTTGGCA TGACACTTGA GTGGTTGGTT CCATACATCC ATATGCAGAT
60

CTTACATTCA CGTGAATATT GCAATGTCCA CTACAGACCA CATATAATAC AGAAATATCT
120

GTAGAACATT ATGCACAGAT ATGCACGATG GACT
154

(SEQ ID NO:3)

AGGATCACAG TTTGTGAAAG GATTTGGTGG AATTGGAGGT ATCTTGCGGT ACGAGTAGAT
60

TCAGGAATGG AATACCAAGG AGGAGATGAC GATTTTTGAC CTTGATGACT ACTAGGTAGT
120

CGACATGGTC CGCAAACGGC TCTCAGCATC ACCAGGAGCA T
161

(SEQ ID NO:4);

TTTTTTAACG GTTCCAACAT TTCACCACAT ATATTTCTGT GCAGTCTAGC CGAGAACGCC
60

ATGTAAATGG GTCACTGCGA GGCAGCGAAC GCAGCAATTT AGTTACTCTC GATCAAGGGA
120

GAAACAACAG TATGAC
136

(SEQ ID NO:5);

CCGTCTGCCA TGCCTCGGAA AATTGAGGAA TCAAGGACTT TCTACTCACA GCGCCGGCGG
60

AAGGATGCAA ATCTGTCAAG ATCAGAAAAA CAGGATAATG TAGTTCAAGG GTCGTGTAGC
120

AGGTAC
126

(SEQ ID NO:6);

TGTTTTGATT TCATCATGCT GTTTAATCTA GCATGTGCTT AGAAGGCTTG TTGGGCAGAG
60

TACAATATCT CCAGCAGTTC TAGAGACCAT TCACCACTGC GA
102

(SEQ ID NO:7);

CACAGTCAGC TCTTTATTGG ACATGTTAAC AAAAGCAGTT TAGTCAAAAA GACCAAAGCC
60

CATGTCATCC TCGGATTCTT CAGATTCTTC CTTCTTTGCT TCTACTTCTT CTCCTCAGCT
120

GGGGCAGCGG CGGCAGATGG AGCAGGACAC AGCGG
156

(SEQ ID NO:8);

-continued

GGCCGCAACTAAAATGGTTT TTAATGGGAA CCAGAGATAT GGTTACAATT ACGTAGTCTG 60

ACACACTCAC ACACACACAC ATACCGTTGC CACCCCCCAA AATATCCATG AGTCAGTCCT 120

GATGTAGGTA CAATACGGTA CCTGGTACGA G 151

(SEQ ID NO:9); and

AGCCTGGCAA GATGGACTCA GGGTGAGCAC AGACAGGATC GCAGGGAGAG GCATATAGCT 60

GACTCTGAGT TCTGACAGCT CTCTGTACCA GTGTACCTGT ATTGTACTAC ATCGATG 117

(SEQ ID NO:10)

or any sequences complementary thereto, derivative sequences having one or more nucleotide substitution or fragments thereof.

It will also be appreciated that the polynucleotide sequences of the present invention define the sequences of polypeptides which are encoded therein. The expression of such polypeptides may itself constitute a useful marker in the investigation of malignant disease. Such polypeptides have some biological role in the development of malignant disease, such as in invasive or metastasis cancer cells, and interference with this function may be useful in therapy of malignant disease.

It will also be appreciated that the aforementioned molecular markers may be determined in a number of different ways. For example, polynucleotide probes may be constructed which are capable of hybridization to any portion of the genomic DNA precursor of the aforesaid RNA sequence including introns and non-coding as well as coding portions of the DNA sequence or to any portion of the cDNA sequence. Such polynucleotide probes comprises a nucleotide sequence capable of hybridization to a sufficient length of the sequence to be determined to ensure that the probe unambiguously detects the sequence of interest.

Thus, in accordance with one embodiment of the present invention there is provided a probe for the diagnosis or prognosis of malignant disease, which comprises a nucleotide sequence capable of hybridizing to a polynucleotide sequence of the present invention or portion thereof, said probe being optionally labeled or marked according to techniques known in the art, such as $^{32}P$, $^{35}S$ fluorescent markers, biotin or even enzyme-label.

The aforementioned molecular markers may also be determined by the use of antibodies, which may be polyclonal or monoclonal, raised to a polypeptide sequence coded for by at least a portion of the genomic DNA sequence or corresponding RNA sequence. The antibody may thus bind to the protein encoded by the aforementioned genomic DNA sequence or corresponding RNA sequence or bind to any fragment of the protein.

Thus, in accordance with one embodiment of the present invention there is provided an antibody which effectively bind to at least a fragment of the polypeptide encoded by the polynucleotide of the present invention. The term "antibody" as used herein includes all immunoglobulins and fragments thereof which contain recognition sites for antigenic determinants of polypeptides of the present invention.

The antibody of the present invention may optionally be labeled or marked as described above for the probes. Also, the antibody of the present invention may be detected by a second antibody which is labeled or marked.

The polynucleotides, polynucleotide probes, polypeptides, and antibodies of the present invention may be used as general markers of invasive or metastatic potential of primary and secondary neoplasms. They may be used for:

1) diagnosis of rhabdomyosarcomas and other malignant neoplasms and their invasive or metastatic potential in tissue samples or cells by Northern blot analysis, PCR, in situ hybridization and immunohistochemistry;

2) diagnostic imaging of invasive or metastatic cancers; and 3) therapy of invasive or metastatic cancers.

DETAILED DESCRIPTION OF THE INVENTION

Figure 1A:
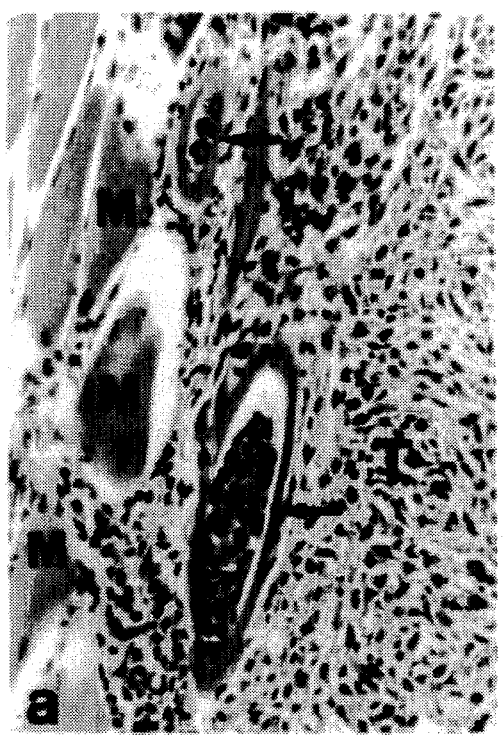
FIG. 1 shows the micrograph of histological sections of intramuscularly transplanted SMF-Ai, SMF-Da and RMS-Bd in syngeneic rats.
Figure 1B:
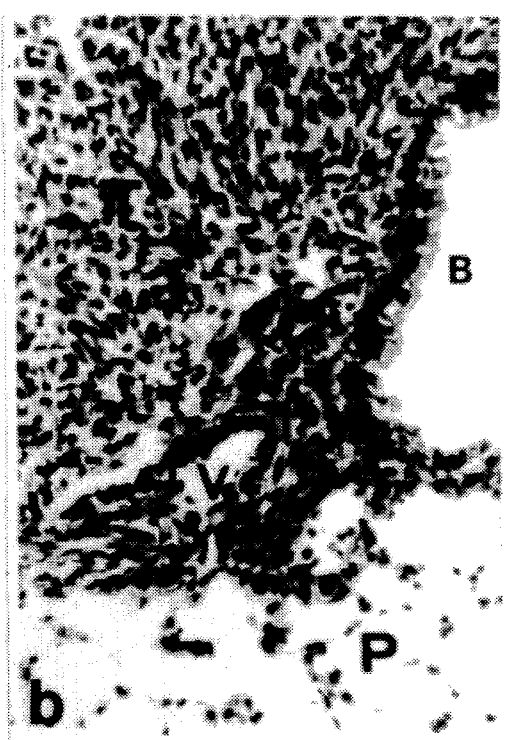
Figure 1C:
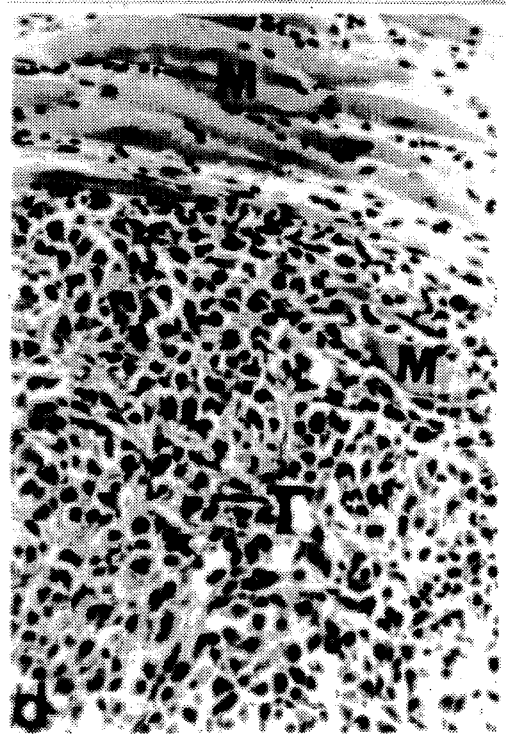
Figure 1D:
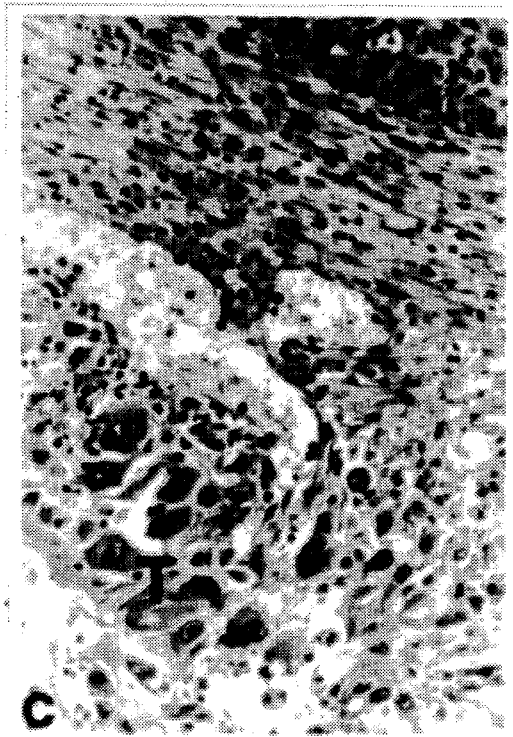

For the purpose of studying invasion and metastasis, a model composed of a number of rat rhabdomyosarcoma cell lines with defined metastasic properties was developed in Dr. F. Babaï laboratory (Babaï F, and Royal A, *Rat myoblastic sarcoma cell lines: A model for the study of invasion, metastasis and myogenic differentiation.* Lab. Investigation, 1994, 90:907–915). These cell lines are SMF-Ai, SMF-Da, RMS-Bg, RMS-Bd and RMS-B. The principal advantage of these cell lines is the fact that the SMF-Ai and RMS-Bg clones always form metastases in syngeneic rats while the SMF-Da and RMS-Bd never do. In addition, the SMF-Ai, RMS-Bg and RMS-Bd are invasive while the SMF-Da clone is not. These characteristics will allow to obtain clear cut results. Also in accordance with the present invention, it was indicated that metastatic cancer cells resemble to leucocytes in their capacity to infiltrate tissues. Leucocytes, like tumor cells are motile and can, under specific circumstances, dissolve and pass through basal lamina (Armstrong PB, *Invasiveness of non-malignant cells.* In: Invasion. Experimental and clinical implications. Mareel MM and Calman KC, ed. Oxford University Press. Oxford, 1984). It is reasonable to expect that, in infiltring cells (tumor cells and macrophages), the same genes will be involved in the process of invasion. Therefore, in accordance with the present invention the peritoneal macrophages is considered as an invasive but non proliferating cell type.

To identify genes implicated in the metastatic potential of Rhabdomyosarcoma, the differential hybridization technique was used to screen a cDNA library prepared from a strongly metastatic rat rhabdomyosarcoma cell line (SMF-Ai) with complementary cDNA probes derived from this cell line and a non-metastatic rat rhabdomyosarcoma cell line SMF-Da. These cell lines have several advantages since they were derived from the same parental line established from a single metastatic nodule. The tumor obtained by the injection of the SMF-Ai cell line in rats skeletal muscle is a highly invasive showing intercellular, translaminar and transcellular invasion. Moreover, the SMF-Da cell line could be consider has a revertant because they have loss their metastatic properties (Babaï F, and Royal A, *Rat myoblastic sarcoma cell lines: A model for the study of invasion, metastasis and myogenic differentiation.* Lab. Investigation, 1994, 90:907–915).

Eight cDNA clones were isolated, which have hybridized differentially between the metastatic SMF-Ai and the non-metastatic SMF-Da cell lines. Clones smf-7, smf-40 and smf-61 are overexpressed in SMF-Ai cell lines and clones smf-4, smf-6, smf-41, smf-42 and smf-44 are overexpressed in SMF-Da cell line. The expression of these clones were analyzed in others rat rhabdomyosarcoma cell lines (RMS-Bg, RMS-Bd and RMS-B) and in transplanted tumors obtained by injection of these cell lines in nude mice. Only smf-6 and smf-7 showed consistent differential expression pattern with all cell lines examined in respect to their metastatic potentials. Differential expression patterns between SMF-Ai and SMF-Da cell lines and in SMF-Ai and SMF-Da transplanted tumors were also observed with smf-42, smf-44, smf-61. In addition, some of the cDNA clones (smf-4, smf-41, smf-42 or smf-44) showed differential expression patterns between rhabdomyosarcoma (metastatic or non-metastatic) and normal skeletal muscle tissue. In accordance with the present invention, the results of this screening is described.

Cell lines

The properties of the SMF-Ai and SMF-Da cell lines derived from a rat metastatic rhabdomyosarcoma have been described in detail by Babaï F, and Royal A (*Rat myoblastic sarcoma cell lines: A model for the study of invasion, metastasis and myogenic differentiation.* Lab. Investigation, 1994, 90:907–915). An others cell line designated RMS-B was obtained from an induced well differentiated primary rhabdomyosarcoma. This parental cell line grows slowly and, after 10 passages, forms occasionally lymph nodes metastasis. The RMS-B line was cloned and two of the clones (RMS-Bg and RMS-Bd) were selected according to their invasive and metastatic potential. Briefly, clone RMS-Bg is highly invasive and metastatic while clone RMS-Bd is slightly invasive but not metastatic.

Cells were grown in DMEM medium (Gibco) with 10% heat inactivated calf serum, 1% of an antibiotic mix (penicillin, 1000 units/ml; streptamycin, 1 mg/ml and gentamycin 50 µg/ml) at 37° C. in the presence of 5% $CO_2$. Once a week, at confluence, the cells were harvested by trypsinisation (Trypsin-EDTA) and re-seeded.

Tumorigenecity and invasiveness of cell lines

Before isolation of cellular RNA, the tumorigenic, invasive and metastatic capacity of SMF and RMS cell lines were tested $5 \times 10^6$ cells were injected in the hind limb skeletal muscle (IM) of three Fisher 344 male rats (Charles River). Tumor growth was evaluated twice a week. Rats were sacrificed when the tumors measured 3–4 cm or when respiratory distress was present. Tumor samples, iliac lymph nodes and lungs were fixed in 100% ethanol and embedded in paraffin for histological study. Sections of transplanted tumors were frozen for RNA preparation.

The biopathologic characteristics of SMF and RMS-B cell lines when RNA was isolated for the preparation of the cDNA library or Northern blot analysis are resumed in Table 1.

TABLE 1

Biopathologic characteristics of SMF and RMS cell lines

|  | SMF-Ai | SMF-Da | RMS-B* | RMS-Bg | RMS-Bd |
|---|---|---|---|---|---|
| Cloned cell line | + | + | − | + | + |
| Tumorigenicity in syngeneic rats | + (3/3) | + (1/3) | + (3/3) | + (3/3) | + (3/3) |
| Invasiveness in syngeneic rats | + | − | + | + | + |
| Invasiveness in vitro (matrigel) | ++++ | − or + | ++ | ++++ | + |
| Metastasis in syngeneic rats | + (3/3) | − (0/3) | (1/3) | + (3/3) | − (0/3) |
| Regression after transplantation | − (0/3) | + (3/3) | − (0/3) | − (0/3) | + (2/3) |
| Tumorigenicity in nude mice | + (3/3) | + (3/3) | + (3/3) | + (3/3) | + (3/3) |
| Metastasis in nude mice | + (2/3) | − (0/3) | − (0/3) | + (2/3) | − (0/3) |

The SMF-Ai and RMS-Bg lines were tumorigenic, highly invasive (intercellular, translaminar and transcellular invasion) and highly metastatic (hematogenic and lymphatic metastasis). SMF-Da (non-invasive) and RMS-Bd (intercellular invasion) were non-metastatic (FIG. 1). A: SMF-Ai cells (T) have infiltrated the intercellular area between skeletal muscle cells (M); Two myofibers (arrows) show transcellular invasion by tumor cells. B: Histological section of a metastatic nodule (T) in the lung of rat injected I.M. with SMF-Ai cells (T). B, bronchiole; V, vessel; P, pulmonary alveols. C: Section of SMF-Da tumor (T) in rat skeletal muscle. Note the absence of muscle invasion and the presence of fibrosis and inflammatory infiltrate composed of mononucleated leucocytes at the periphery of the tumor and between tumor cells. D: Section of RMS-Bd tumor (T) in rat skeletal muscle (M) showing slight intercellular invasion and the presence of the inflammatory infiltrate at the periphery of the tumor.

RMS-B cell line was invasive (intercellular) and slightly metastatic to lymph node. In vitro invasiveness was examined by determining the level of tumor cell infiltration in reconstituted basal lamina (non-diluted matrigel) using modified Boyden chamber (Babaï F, and Royal A, *Rat myoblastic sarcoma cell lines: A model for the study of invasion, metastasis and myogenic differentiation.* Lab. Investigation, 1994, 90:907–915). This assay shows deep infiltration of SMFAi and RMS-Bg cells and superficial proliferation without deep infiltration or invasion by SMF-Da cells in semithin sections of epon embedded specimen.

Isolation and analysis of RNA

Total cellular RNA was isolated by the technique of guanidium isothiocyanate (Sambrook J, Fritsch EF, and Maniatis T. *Molecular cloning: A laboratory manual,* second edition, Cold Spring Harbor Laboratory Press, 1989) or by a modification of this technique (Croze F et al., *Endocrinology,* 1990, 127:2665–2672). For the preparation of polyadenylated RNA, total RNA preparations were passaged twice through oligo(dt)-cellulose (type 7, Pharmacia). For the Northern blot analysis, total RNA was fractionated on a 1.5% agarose-formaldehyde gels in denaturing conditions (Sambrook J, Fritsch EF, and Maniatis T. *Molecular cloning: A laboratory manual,* second edition, Cold Spring Harbor Laboratory. Press, 1989). To prepare the probes, each plasmid (pCR) was digested by EcoR1 and the insert was eluted on agarose gel. Inserts were labeled with [$\alpha^{32}$P] dCTP using oligolabeling kit (Pharmacia). Blots were scanned using Imagequant™ (Personal Densitometer, Molecular dynamics).

Preparation of the cDNA library

For the preparation of the cDNA library of the SMF-Ai cell line, different commercial kits were used to optimize the conditions of the cDNA library constructions. Two µg of polyadenylated RNA from SMF-Ai cell line were used to synthetized the first strand cDNA with an oligo(dt) primer according to the BRL's (BRL Lite Technologies) superscript cDNA synthesis. The second strands cDNA were performed using the Amersham's cDNA synthesis system. The cDNA were ligated with EcoR1-Not1 adaptor (Pharmacia) in the EcoR1 site of the λgt10 (Stratagene).

Differential screening and polymerase chain reaction (PCR) conditions cDNA library of the SMF-Ai cell line was screened twice on duplicate filters using cDNA probes prepared from SMF-Ai and SMF-Da polyadenylated RNA. These probes were synthesized with 50 µCi [$\alpha^{32}$P] dCTP according to the first strand synthesis method of BRL's superscript cDNA synthesis. Phage from differential clones were picked up and transferred in 200 µl of sterile water. DNA was recovered after 3 cycles of freeze-thaw (clontech) and was amplified by PCR using λgt10 primers SEQ ID NO:11) (SEQ ID NO:12). The PCR reaction was performed with 20 µl of DNA from the freeze-thaw reaction; 100 ng of each primer; 0,25 mM dNTP; 50 mM KCL; 10 mM Tris-HCl pH=8; 0,5 mM MgCl$_2$; 0,01% of gelatin and 2.5 units of taq DNA polymerase (Perkin-Elmer) in a total volume of 50 µl. PCR conditions were 1 cycle with denaturation at 95° C. for 3 min., annealing at 50° C. for 1 min. and elongation at 72° C. and 29 cycles with denaturation at 95° C. for 1 min., annealing at 50° C. for 1 min. and elongation at 72° C. for 1 min. The PCR products were electrophoresed on 1.2% agarose gel, transferred on nylon membrane as described by Sambrook et al. (*Molecular cloning: A laboratory manual,* second edition, Cold Spring Harbor Laboratory Press, 1989). These blots were hybridized with cDNA probes synthetized with 2 µg of polyadenylated RNA from SMF-Ai and SMF-Da cell lines. After the selection of differential clones, the PCR products were cloned in the pCR vector according to the TA™ cloning kit (Invitrogen) and plasmid DNA were prepared with the midi-prep™ kit of Qiagen. Sequenase version 2.0 (U.S.B.) was employed for nucleotide sequencing. Primers SP6 or T7 were utilized with the denaturated DNA templates in the annealing mixture.

Figure 2:
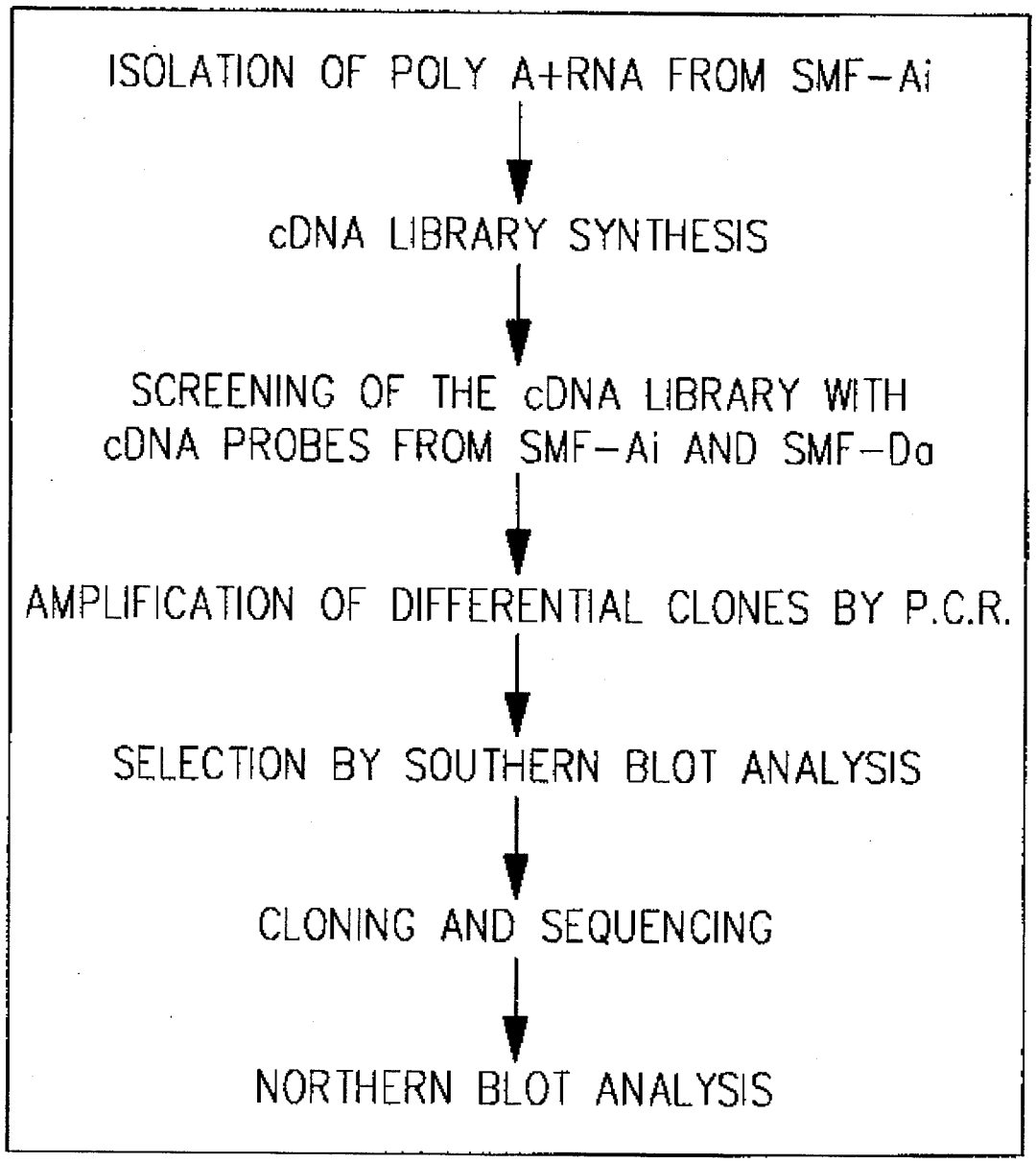
FIG. 2 illustrates the schematic outline of the strategy for the differential hybridizations between the metastatic SMF-Ai cell line and the non-metastatic SMFDa cell line.
Figure 3A:
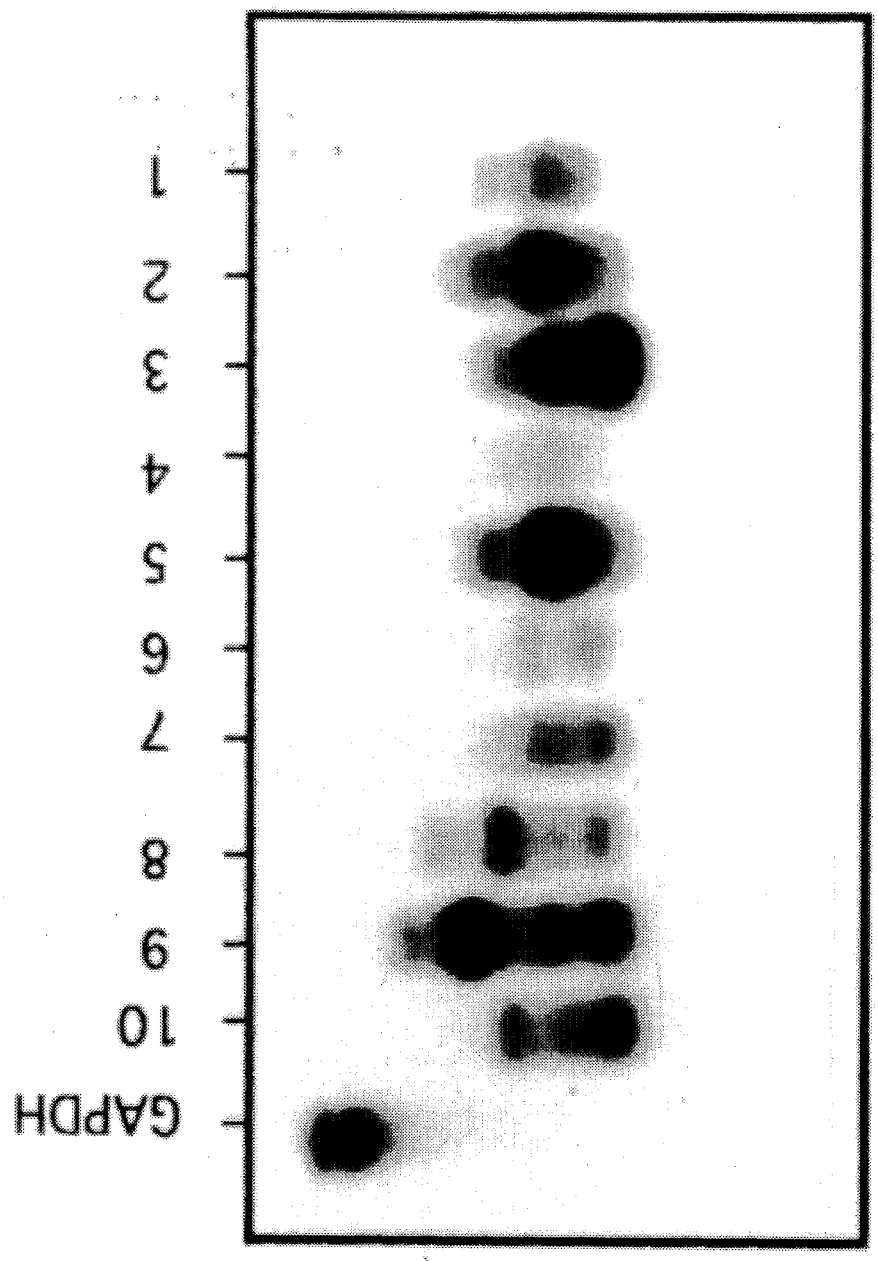
FIG. 3 shows the selection of differential clones by southern blot analysis.
Figure 3B:
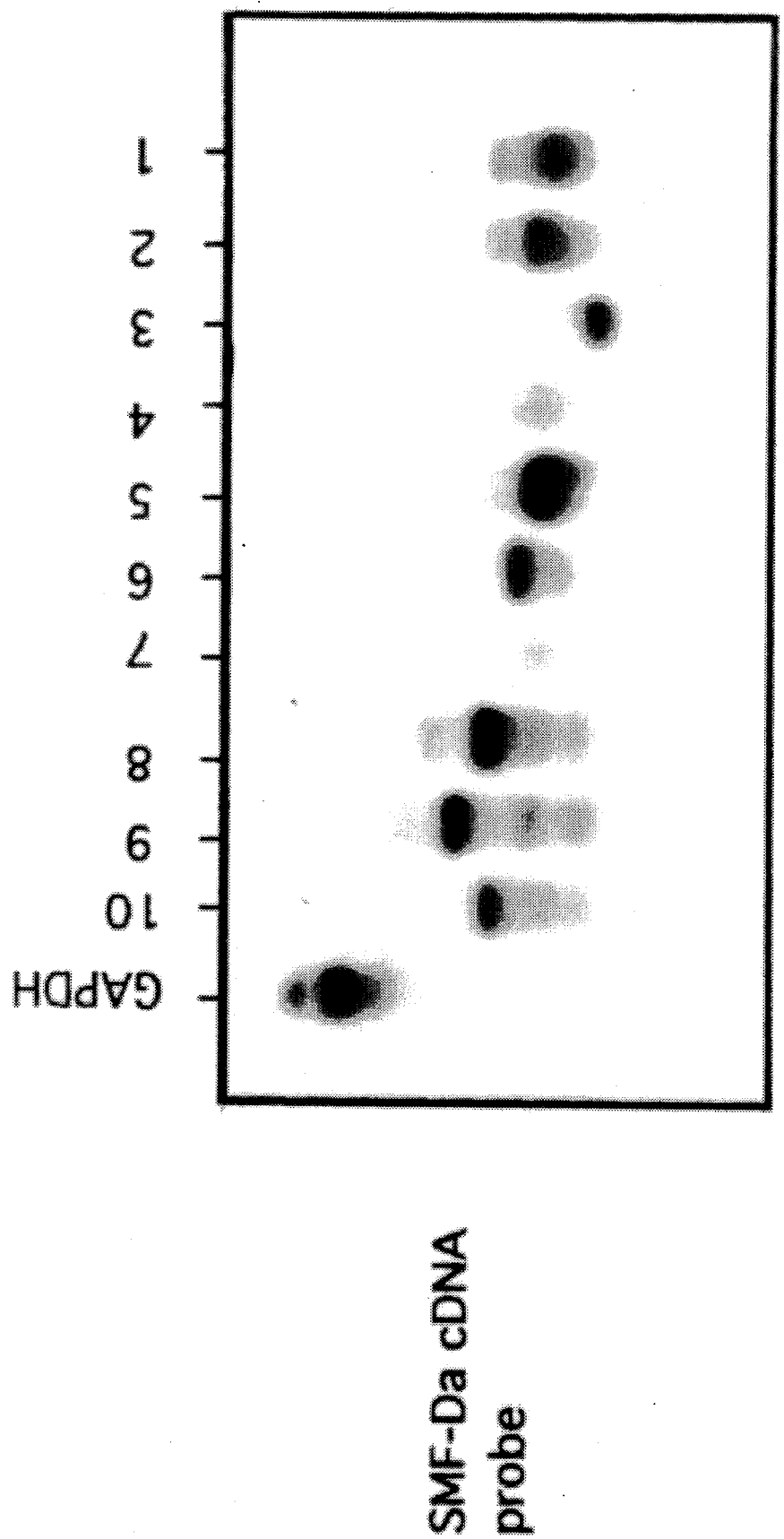
Figure 4G:
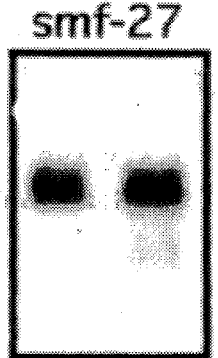
FIG. 4 is the Northern blot analysis of the smf clones on RNA from the SMF-Ai cell line and the SMF-Da cell line.
Figure 4H:
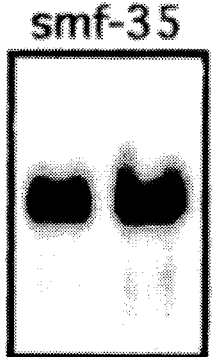
Figure 4I:
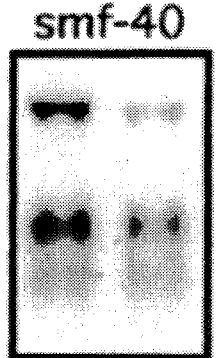
Figure 4J:
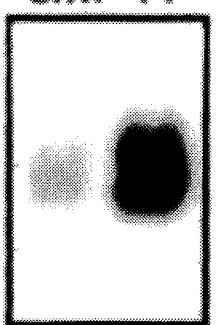
Figure 4K:
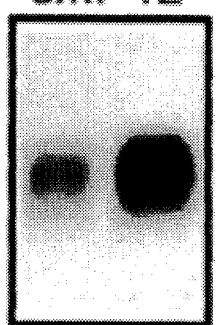
Figure 4L:
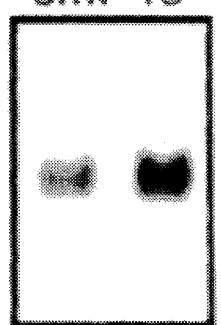
Figure 4M:
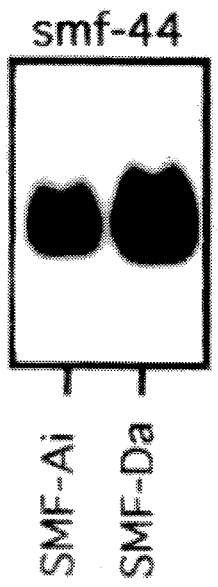
Figure 4N:
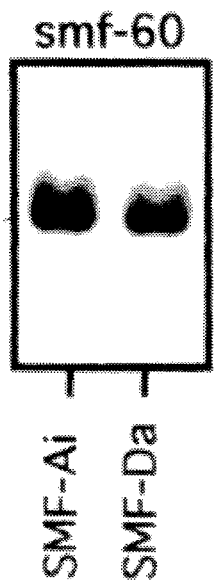
Figure 4O:
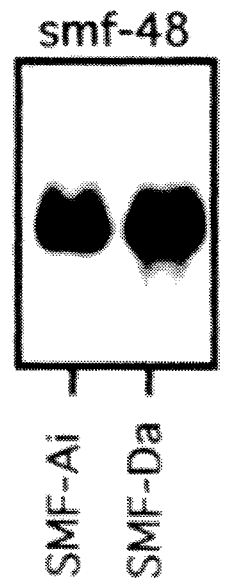
Figure 4P:
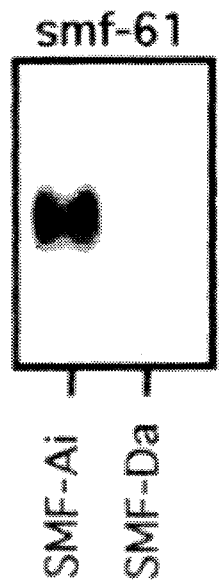
Figure 4Q:
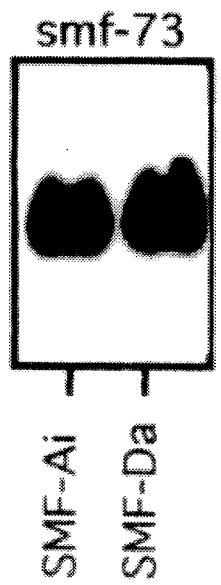
Figure 4R:
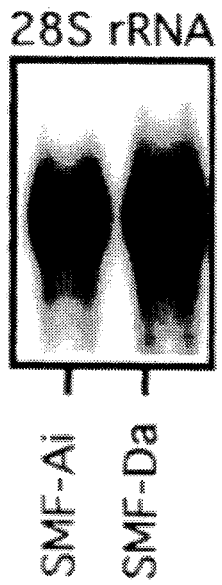
Figure 5A:
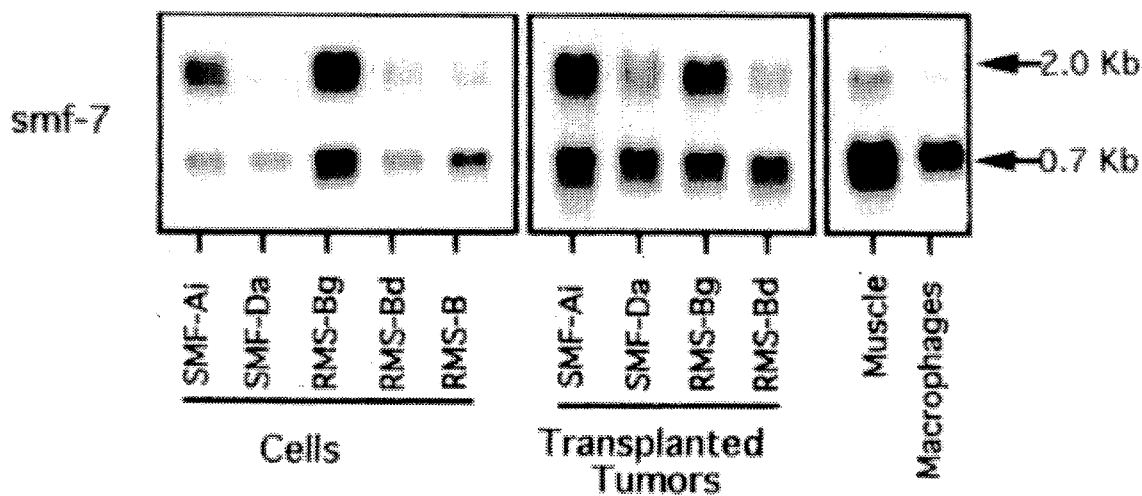
FIG. 5 is the Northern blot analysis of the smf clone overexpressed in the SMF-Ai.
Figure 5B:
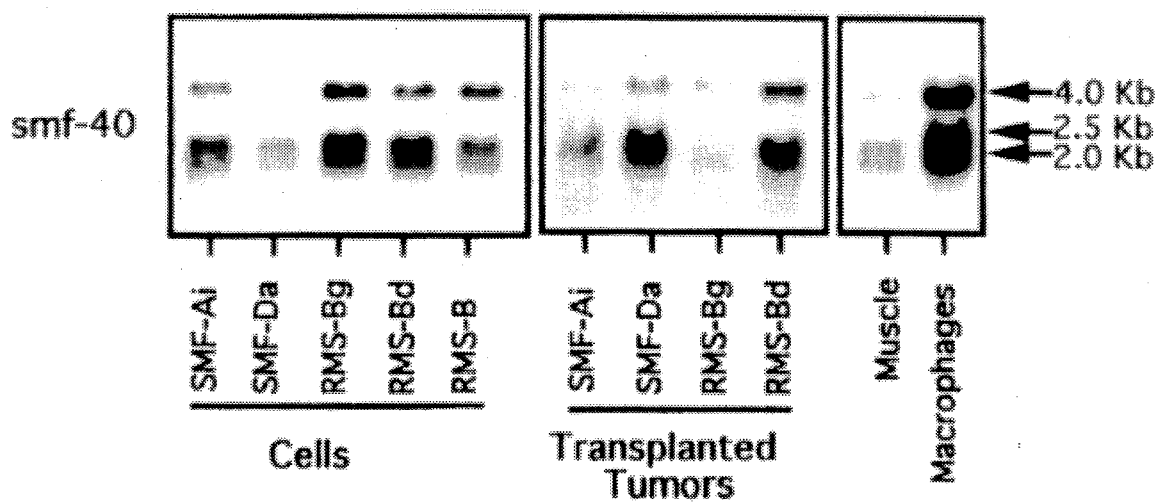
Figure 5C:
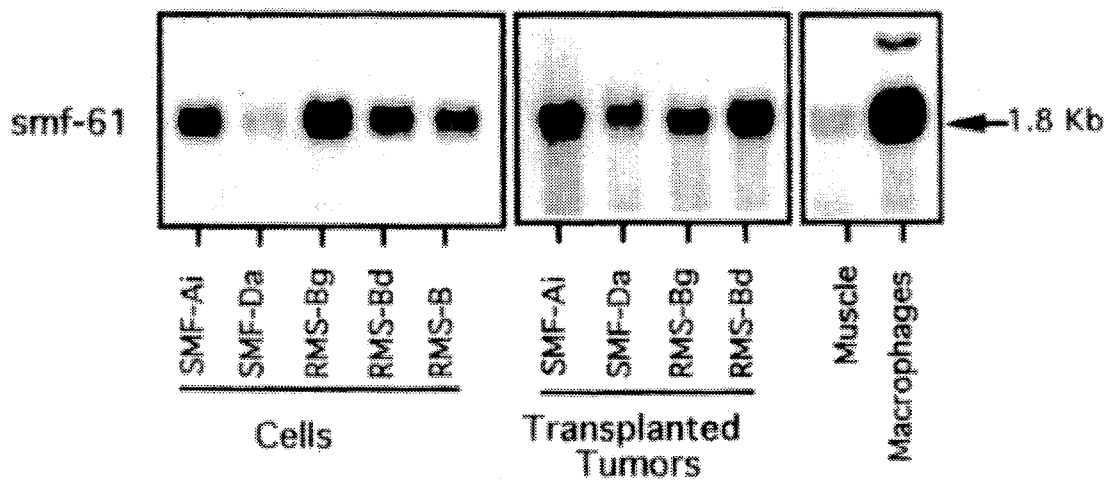
Figure 5D:
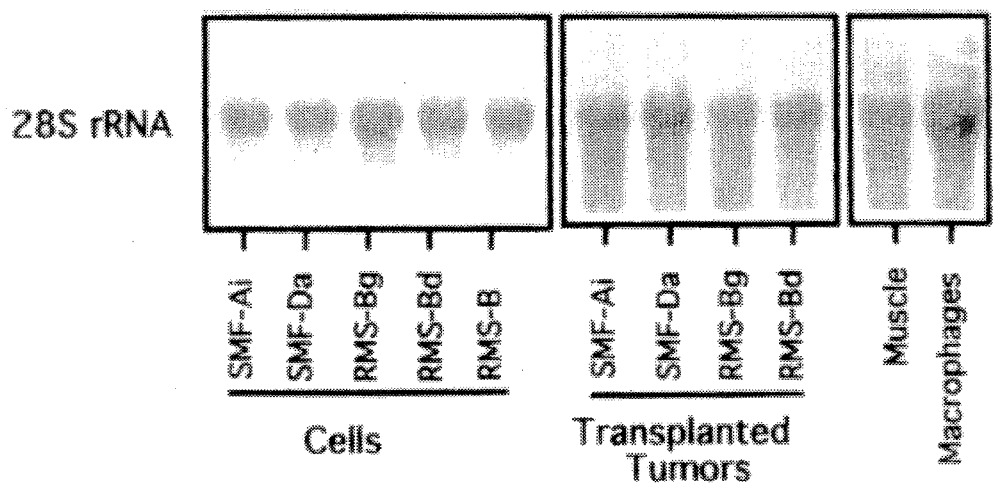
Figure 6A:
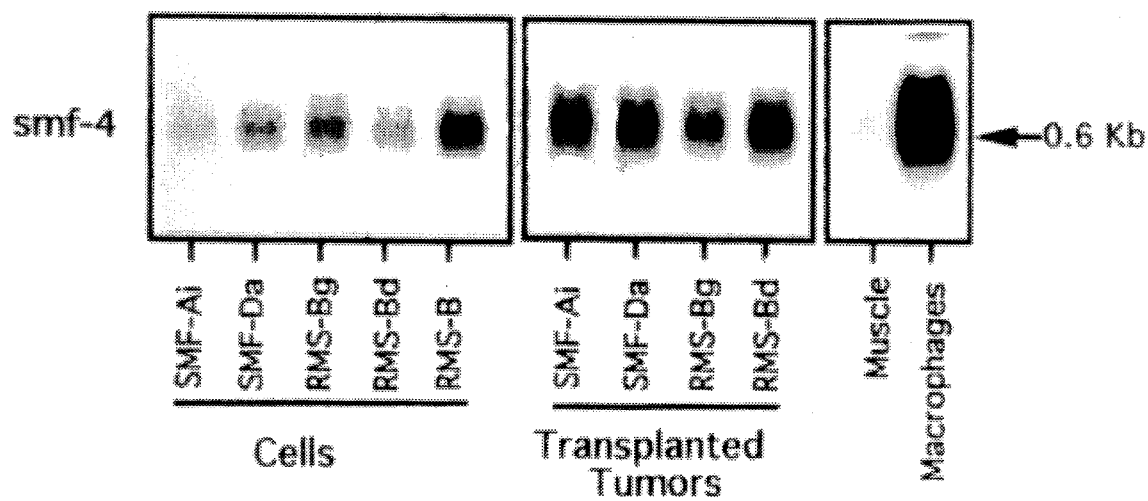
FIG. 6 is the Northern blot analysis of the smf clones overexpressed in the SMF-Da.
Figure 6B:
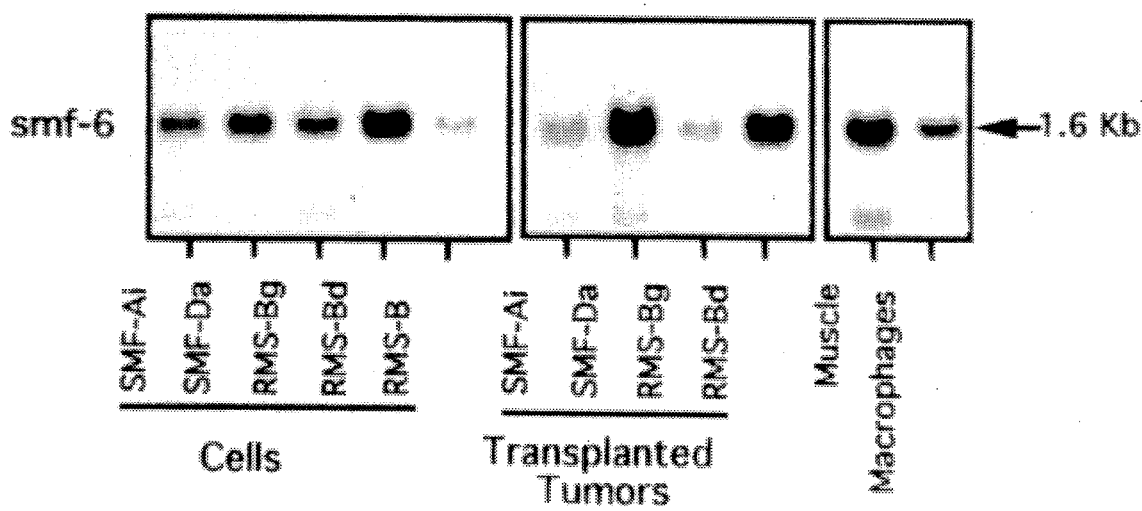
Figure 6C:
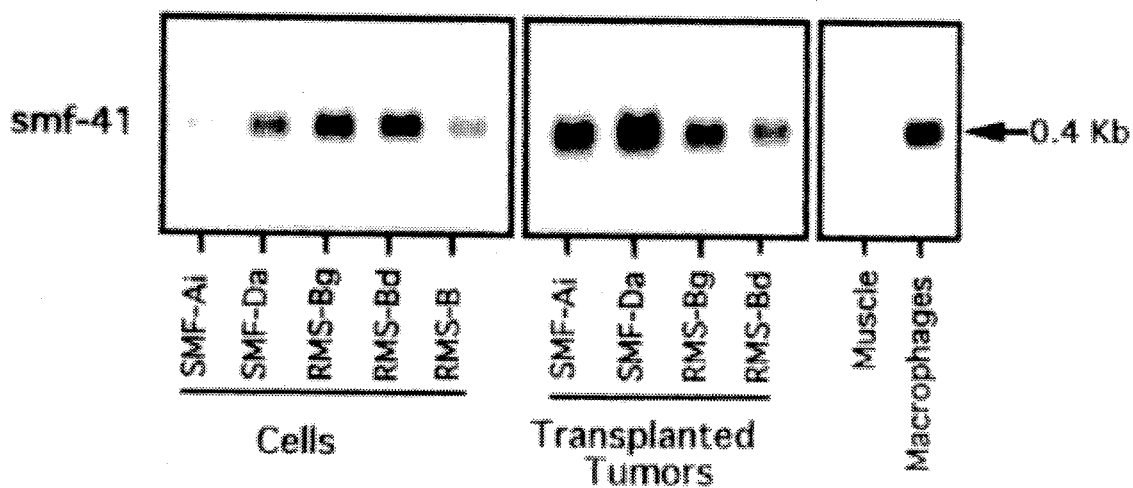
Figure 6D:
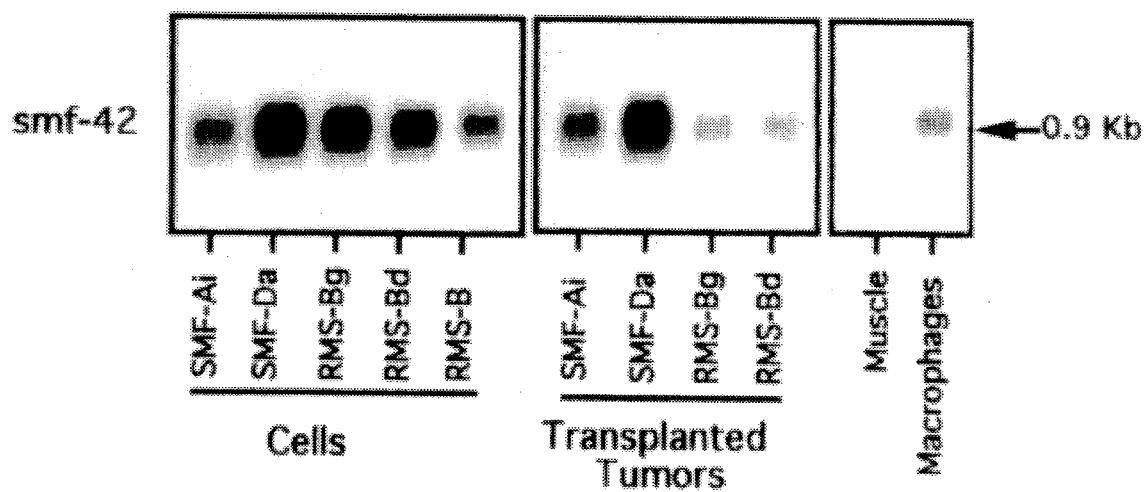
Figure 6E:
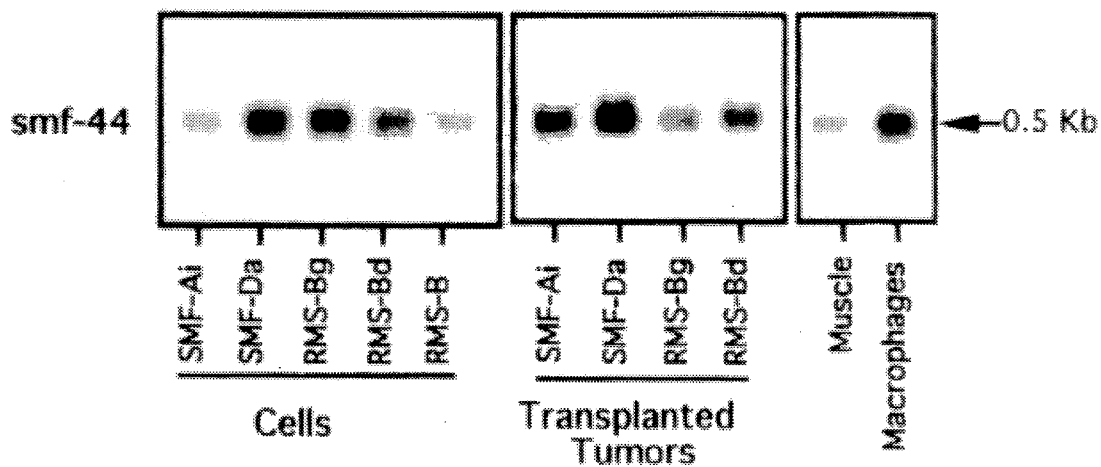
Figure 6F:
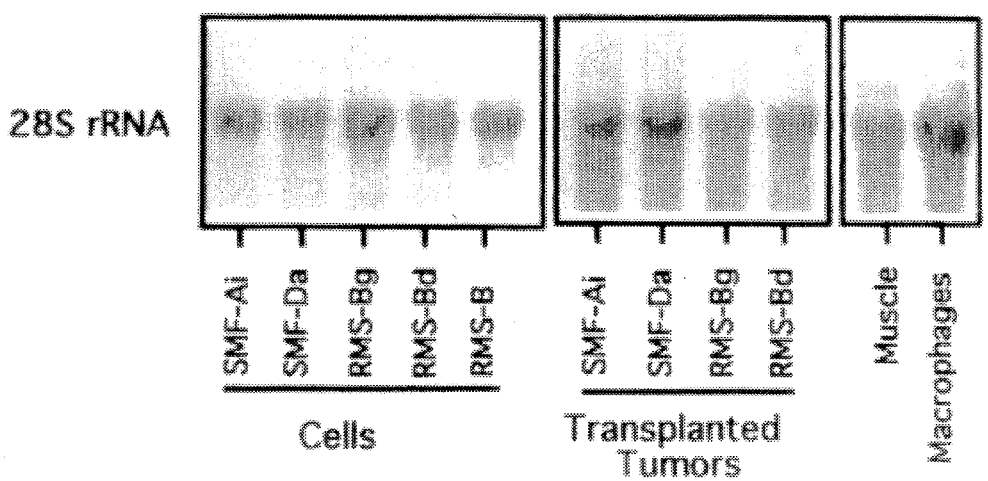

The strategy for the differential screening is shown in FIG. 2. Over 3×10$^5$ recombinant phages of the cDNA library of SMF-Ai polyadenylated RNA were screened twice on duplicate filters using cDNA probes prepared from SMF-Ai and SMF-Da polyadenylated RNA. After 2 rounds of differential screening, 97 candidate differentially expressed clones were amplified by PCR. These clones were designated smf because they were isolated from the SMF cell lines. A southern blot analysis of the PCR products (see Materials and Methods) was performed to confirm the differential expression of these clones (FIG. 3). Twenty µl of the PCR products were electrophoresed in duplicate on 1.2% agarose gel, transferred on nylon membrane and hybridized with cDNA probes synthetized with 2 µg of polyadenylated RNA from SMF-Ai or SMF-Da as described above. This figure show the clone smf-1 to smf-10 and GAPDH was used as control.

Only 33 clones showed consistent differential hybridization between the metastatic cell line SMF-Ai and the non-metastatic cell line SMF-Da. The PCR products were cloned in the pCR vector (Invitrogen).

Partial nucleotide sequence and Northern blot analysis of the cDNA clones in SMF-Ai and SMF-Da cell lines.

Partial DNA sequences were performed on these clones to determined the type of these cDNA clones. About 200 to 400 bases were sequenced and compared to Genbank™ and EMBL™ databases with the program blast. On the 33 clones, 17 were unique and were further characterized by Northern blot analysis on total RNA isolated from SMF-Ai and SMF-Da cell lines (FIG. 4). Twenty µg of total RNA prepared from the rat rhabdomyosarcoma SMF-Ai and SMF-Da cell lines were hybridized with $^{32}$P-labeled smf probes derived as indicated above each blot.

TABLE 2

| SEQ. ID. No. | cDNA clone | Homology search alignment result | homology (%) | Length of the cDNA clone (Kb) | numbers of sequenced nucleotides | Length of mRNA (Kb) | Overexpression in SMF-Ai or SMF-Da cell lines |
|---|---|---|---|---|---|---|---|
| 1 | smf-4 | Beta-2-microglobulin | 93 | 0.6 | 174 | 0.6 | SMF-Da |
| 2–3 | smf-6 | Lactate dehydrogenase | 93 | 0.9 | 149–154 | 1.6 | SMF-Da |
| 4 | smf-7 | no significant homology* | — | 0.5 | 289 | 2 & 0.7 | SMF-Ai |
| 5–6 | smf-40 | Human TB3-1 | 81 | 0.7 | 161–136 | 4, 2.5 & 2 | SMF-Ai |

TABLE 2-continued

| SEQ. ID. No. | cDNA clone | Homology search alignment result | homology (%) | Length of the cDNA clone (Kb) | numbers of sequenced nucleotides | Length of mRNA (Kb) | Overexpression in SMF-Ai or SMF-Da cell lines |
|---|---|---|---|---|---|---|---|
| 7 | smf-41 | Ribosomal protein L38 | 88 | 0.35 | 126 | 0.35 | SMF-Da |
| 8 | smf-42 | Ribosomal protein S4 | 82 | 0.5 | 102 | 0.9 | SMF-Da |
| 9 | smf-44 | Acidic ribosomal phosphoprotein P1 | 97 | 0.6 | 156 | 0.47 | SMF-Da |
| 10–11 | smf-61 | Human fus | 71 | 0.5 | 151–117 | 1.8 | SMF-Ai |

The results showed that only eight clones hybridized differentially between the metastatic cell line SMF-Ai and the non-metastatic cell line SMF-Da (FIG. 4 and Table 2). These clones are smf-4, smf-6, smf-7, smf-40, smf-41, smf-42, smf-44 and smf-61. The smf-4 cDNA is homologous to the beta-2-microglobulin (Mauxion F et al., *Nucleic Acids Res.*, 1987, 15:7638). The smf-6 cDNA corresponds to the lactate dehydrogenase (Matrisian LM et al., *Nucleic Acids Res*, 1985, 13:711–726). The smf-40 cDNA is homologous to the human TB3-1 gene (Grenett HE et al., *Gene*, 1992, 110:239–243). The smf-41 cDNA corresponds to the ribosomal protein L38 (Kuwano Y et al., *Biochem. Biophys. Res. Commun.*, 1991, 175:551–555). The smf-42 corresponds to the ribosomal protein S4 (Devi KR et al., *Biochem. Biophys. Acta*, 1989, 1008:258–262). The smf-44 cDNA corresponds to the acidic ribosomal phosphoprotein P1 (Wool IG et al., *Biochimie*, 1991, 73:861–870). The cDNA clones smf-7 and smf-61 have no significant homology to known sequences in hat. However, there is 71% homology between smf-61 cDNA clone and human fus gene (Rabbitts, T. H. et al., *Nature Genetics*, 1993, 4:175–180). The expression of the eight isolated cDNA clones were assessed in total RNA from SMF-Ai, SMF-Da, RMS-Bg, RMS-Bd, RMS-B cell lines, in SMF-Ai, SMF-Da, RMS-Bg and RMS-Bd transplanted tumors, in muscle and in macrophages.

The present invention will be more readily understood by referring to the following examples which are given to illustrate the invention rather than to limit its scope.

EXAMPLE I

Clones overexpressed in SMF-Ai metastatic cell line

The clones smf-7, smf-40 and smf-61 are overexpressed in SMF-Ai cell line. The results of the Northern blots with others rat rhabdomyosarcoma cell lines, in transplanted tumors, in muscle and in macrophages are presented in FIG. 5 and the densitometry data of the Northern blots are showed in Table 3. Ten μg of total RNA prepared from rat rhabdomyosarcoma cell lines, transplanted tumors and others tissues as indicated under the blots, were hybridized with the differential $^{32}$P-labeled smf probes as indicated above each blot.

TABLE 3

Densitometry data of the Northern blots

| cDNA clone | Cells in vitro | | | | | Transplanted tumors | | | | | |
|---|---|---|---|---|---|---|---|---|---|---|---|
| | SMF-Ai | SMF-Da | RMS-Bg | RMS-Bd | RMS-B | SMF-Ai | SMF-Da | RMS-Bg | RMS-Bd | Muscle | Macrophage |
| smf-4 | 1.0 | 4.5 | 3 | 2 | 6 | 7 | 6 | 6 | 9 | 2 | 40 |
| smf-6 | 9.0 | 20 | 8 | 34 | 2 | 3.5 | 26 | 3 | 27 | 27.5 | 5 |
| smf-7 | 7.5 | 0.8 | 12.5 | 1.4 | 1.4 | 8.5 | 2.5 | 8.6 | 2 | 3.5 | 0.8 |
| smf-40 | 3.0 | 0.65 | 7 | 3 | 5 | 0.3 | 1 | 0.7 | 3.4 | 0.9 | 11 |
| smf-41 | 4.0 | 12 | 12 | 14 | 6.5 | 13 | 16 | 13 | 9 | 3 | 9 |
| smf-42 | 4.0 | 25 | 11 | 7 | 3 | 14 | 36 | 8.5 | 6.8 | 2.3 | 5.2 |
| smf-44 | 3.5 | 11 | 15 | 18 | 3 | 12 | 20 | 6 | 10 | 4.5 | 9.5 |
| smf-61 | 12 | 0.75 | 23 | 7 | 5 | 10 | 2.5 | 7 | 16 | 2 | 40 |

The clone smf-7 hybridized to a 0.7 and 2 Kb mRNA. The expression of the 0.7 Kb mRNA remains similar between the different cell lines. However, the 2 Kb mRNA is overexpressed in SMF-Ai, RMS-Bg cell lines and in SMF-Ai and RMS-Bg transplanted tumors than in SMF-Da, RMS-Bd cell lines, in SMF-Da and RMS-Bd transplanted tumors, in muscle and in macrophages. The clone smf-40 hybridized to a 2.0, 2,5 and 4 Kb mRNA. These mRNA are overexpressed in SMF-Ai, RMS-Bg and RMS-Bd cell lines than in SMF-Da cell line. In contrast, the expression of the smf-40 is higher in SMF-Da and RMS-Bd transplanted tumors than in SMF-Ai and RMS-Bg transplanted tumors. The clone smf-40 is highly expressed in macrophages. The clone smf-61 is overexpressed in SMF-Ai, RMS-Bg and RMS-Bd cell lines, in SMF-Ai, RMS-Bg and RMS-Bd transplanted tumors than in SMF-Da cell line and SMF-Da transplanted tumors. The smf-61 is highly expressed in macrophages.

Clones smf-7 (2 Kb mRNA), smf-40 and smf-61 are overexpressed in the metastatic SMF-Ai cell line (FIGS. 4 and 5 and Table 3). Expression of the 2 Kb RNA of the clone smf-7 correlated well with the metastatic potential and is overexpressed in metastatic cell lines (SMF-Ai and RMS-Bg) comparatively to the non-metastatic cell lines (SMF-Da and RMS-Bd) in vitro and in vivo with transplanted tumors. Furthermore, expression of the 2 Kb RNA is low in muscle and in macrophages. The smf-7 clone have no significant homology with known sequences.

For smf-61 clone, differential expression is less observed between RMS-Bg cell line and RMS-Bd cell line than SMF-Ai and SMF-Da cell lines in vitro and in vivo but smf-61 is highly expressed in macrophages. In fact, RMS-Bd cell line is non-metastatic but has an invasive potential (Table 1). This indicates that smf-61 clone may be related to the invasive potential of tumor cells. The smf-61 cDNA has no significant homology with known sequences. However, it shows 71% homology with the human fus gene observed in human liposarcoma tumor lines carrying the specific t (12;16) (q13;p11) translocation, the presence of a potential fusion protein between CHOP and a novel gene, designated as fus, on chromosome 16 (Rabbitts, T. H. et al., *Nature Genetics*, 1993, 4:175–180). They suggested that gene and protein fusion will be the most common molecular event resulting from chromosome abnormalities in solid tumors.

A preliminary study on expression of smf-7 and smf-61 clones in human cancer cell lines showed highly mRNA expression in Northern blot analysis of a rhabdomyosarcoma and an epidermoid carcinoma cells. This finding suggested the presence of homologous genes for smf-7 and smf-61 clones in human cancers.

However, it is necessary to clone and sequence, the complete cDNA or a more longer clone to be sure that smf-7 and smf-61 correspond to an unknown genes. The clone smf-40 is a rat homologue of the human TB3-1 gene (Grenett HE et al., *Gene*, 1992, 110:239–243). Grenett et al. (Grenett HE et al., *Gene*, 1992, 110:239–243) suggested that this gene may play a role in the accurate recognition of nonsense codons in mammalian cells as a termination factor because this cDNA demonstrated a strong structural similarity to yeast omnipotent suppressor 45. In Northern blot analysis of smf-40, we detected three different RNA of 2.6, 2.8 and 4 Kb. The clone smf-40 is overexpressed in SMF-Ai, RMS-Bg and RMS-Bd cell lines comparatively to the SMF-Da cell line (FIGS. 4 and 5 and Table 3). However, expression of smf-40 is higher in SMF-Da and RMS-Bd transplanted tumors than in SMF-Ai and RMS-Bg transplanted tumors (FIG. 5). This could be explained by macrophages infiltration of transplanted tumors and high expression of smf-40 in macrophages.

The polynucleotides probes, polypeptides and antibodies prepared from the clones smf-7, smf-61 and smf-40 may be used as general markers of invasive and/or metastatic potential of primary and secondary neoplasms. They may also be used for the diagnosis of rhabdomyosarcomas and other malignant neoplasms and their invasive or metastatic potential, in tissue samples or cells by Northern blot analysis, PCR, in situ hybridization and immunohistochemistry. They may also be used for the diagnostic imaging of invasive or metastatic cancers and gene therapy of metastatic cancers.

EXAMPLE II

Clones overexpressed in SMF-Da non-metastatic cell line

The clones smf-4, smf-6, smf-41, smf-42 and smf-44 are overexpressed in SMF-Da cell line. The results of the Northern blots with others rat rhabdomyosarcoma cell lines, in transplanted tumors, in muscle and in macrophages are presented in FIG. 6 and the densitometry data of the Northern blots are showed in Table 3, above. Ten μg of total RNA prepared from rhabdomyosarcoma cell lines, transplanted tumors and others tissues as indicated under the blots, were hybridized with the differential $^{32}$P-labeled smf probes as indicated above each blot.

The clone smf-4 is overexpressed in SMF-Da and RMS-Bg cell lines comparatively to SMF-Ai and RMS-Bd cell lines. Expression of smf-4 is similarly high in transplanted tumors and low in normal muscle tissue. It is highly expressed in macrophages. The clone smf-6 is overexpressed in SMF-Da, RMS-Bd cell lines as well as in SMF-Da and RMS-Bd transplanted tumors than in SMF-Ai, RMS-Bg cell lines and in SMF-Ai and RMS-Bg transplanted tumors. The clone smf-6 is highly expressed in muscle. In macrophages, smf-6 is expressed at the same level than in metastatic cell lines. The clone smf-41 is overexpressed in all transplanted rhabdomyosarcoma and in all cell lines except in SMF-Ai, RMS-B cell lines and in muscle. The clone smf-42 is overexpressed in SMF-Da cell line and in SMF-Da transplanted tumors than in SMF-Ai, RMS-Bg, RMS-Bd and RMS-B cell lines, in SMF-Ai, RMS-Bg and RMS-Bd transplanted tumors, in muscle and macrophages. The clone smf-44 is overexpressed in SMF-Da, RMS-Bg and RMS-Bd cell lines than in SMF-Ai and RMS-B cell lines. In transplanted tumors, the expression of smf-44 is slightly higher in SMF-Da tumor than in SMF-Ai, RMS-Bg and RMS-Bd tumors.

The clones smf-4, smf-6, smf-41, smf-42 and smf-44 are overexpressed in SMF-Da cell line (FIGS. 4 and 6 and Table 3). The clone smf-4 corresponded to beta-2-microglobulin gene. This gene encoded a small protein of 12 KDa which are associated with a 40–50 KDa product of major histocompatibility complex (Michaelson J, *Immunogenetics*, 1983, 17:219) and are involved in the expression of MHC class I heavy chains (Ljunggren H-G et al., *J. Immunol.*, 1990, 145:380–386). The product of this gene may be involved in the rejection process of the SMF-Da tumor when the cells are injected in the syngeneic rats. However, high level of expression of this gene is also observed with RMS-Bg cell line which is not rejected after the injection of these cells in syngeneic rat (FIG. 6)- Expression of smf-6, corresponded to the lactate dehydrogenase (a glycolytic enzyme), is slightly higher in the non-metastatic cell lines SMF-Da and RMS-Bd than in the metastatic cell lines SMF-Ai and RMS-Bg (FIG. 6). Differential expression become more evident in transplanted tumors obtained by the injection of these cells in nude mice (FIG. 6). The clone smf-6 is expressed at the same level in rat skeletal muscle than SMF-Da and RMS-Bd cell lines. In macrophages, the clone smf-6 is expressed at the same level than SMF-Ai, RMS-Bg and RMS-B cell lines. The level of smf-6 expression correlated with the differentiation state of cell lines since the SMF-Da and RMS-Bd cell lines are in a more advanced differentiation state than SMF-Ai and RMS-Bg cell lines. The role of this gene in the metastatic process remains to be determined but cancer cells have often a high glycolytic rate (Argiles JM et al., *Medical Hypotheses*, 1990, 32(2):151–155). A number of clones corresponded to genes encoded for ribosomal protein or proteins associated with the translationnal machinery have been isolated. Clones smf-41, smf-42 and smf-44 corresponded to ribosomal protein S4, L38 and acidic ribosomal phosphoprotein P1 respectively. Elvin et al., (Elvin P et al., *Br. J. Cancer*, 1988, 57:36–42) have isolated an other member of P-proteins, the ribosomal phosphoprotein P2. This group found that the expression of pLM59 (P2 gene) is enhanced in a liver metastasis compared with a primary colon carcinoma and normal colonic mucosae (Elvin P et al., *Br. J. Cancer*, 1988, 57:36–42). In contrast, Sharp et al., (*Br. J. Cancer*, 1990, 61:83–88) found that the abundance of pLM59-homologous mRNA in. human breast fibroadenomas (non-metastatic) was significantly higher than in human breast carcinoma (highly metastatic). Pogue-Geile et al. (*Mol. and Cell. Biol.*, 1991, 11:3842–3849) described the abundance of S3 ribosomal protein in human colorectal carcinoma and adenomatous polyps. They suggested that there is an increase in the synthesis of ribosomes in colorectal tumors and that this increase is an early event in colon neoplasia. Kondoh et al. (*Cancer Res.*, 1992, 52:791–796) observed high level of expression of the S19 ribosomal protein combined with low expression of HLA-1 in highly malignant colon carcinoma. Enhanced expression of ribosomal proteins could be indicative of higher rate of overall translation which may be related to the proliferation rate of the cells (Sharp MGF et al., *Br. J. Cancer*, 1990, 61:83–88). However, we believe that is not the case here since metastatic cell line SMF-Ai have a higher proliferation rate than SMF-Da. Our results suggest that there is an increase in the expression of some ribosomal proteins (L38, S4 and acidic phosphoprotein P1) at various degree, in rhabdomyosarcoma as compared with normal skeletal muscle (FIG. 6 and Table 3). However, the correlation with the metastatic potential is not always consistent.

The RMS-B parental cell line is established from a primary induced well differentiated RMS. The expression of some cDNA clones in this cell lines if compared to their metastatic (RMS-Bg) and non-metastatic (RMS-Bd) clones is variable and without correlation with its metastatic potential. This discrepancy and variation may be explained by the heterogeneous subpopulation of this line. The various proportion of metastatic and non-metastatic cells present in the line and the interaction of these sub-populations between them and environmental factors can modify the expression of mRNA detected by Northern blot.

Our observations suggested that some of these cDNA clones may be use for the study of differentiation state of rhabdomyosarcomas (as smf-6 for example) or neoplastic transformation (as smf-4, smf-41, smf-42 and smf-44 for example) in skeletal muscle tissues.

In conclusion, the isolation of eight cDNA clones differentially expressed between metastatic and non-metastatic SMF cell lines were described in accordance with the present invention. Only clones smf-6, smf-7 and smf-61 showed consistent differential expression pattern with all cell lines examined in respect to their metastatic or invasive potentials and two of them (smf-7 and smf-61) show no significant homology with know gene. Much more work is needed such Northern blot analysis with other tumors and normal tissues, transfection with complete cDNA clones and in situ hybridization or immunohistochemistry to determine the function of these clones in the metastatic or reversion process.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A polynucleotide sequence which is differentially expressed in invasive or metastasis cancer cells during malignant tumore progression of cancer, wherein said sequence is selected from the group consisting of:

CTATCATTTA TCCACAAGAT AGATAGCAAT
    GAGCACACCA TCTCCTCATA TCTTACCCTA 60
AATATTTATG CATGTTTAAA AAATTGGAGA
    CTAATATCCT AGATTTCCGG AATAATAAAG 120
CTTCAATGAG TGGTTTTGAT CAGAATAATA
    AATATGGTTA AGAACAAGAA AAAA 174
(SEQ ID NO:1);

GGCCGCTGCA TACGAAGTGA TCAAGCTGAA
    GGTTACACAT CCTGGGCCAT TGGCTCTCCG 60
TGGCAGACTT GGCCGAGAGC ATAATGAAGA
    ACTAGGCGGG TCGATCCATT TCCGACATGA 120
TTAGGTCTCT ATGGATCAAG GAGGATCTG 149
(SEQ ID NO:2);

TTTGGTGTTT TTCCTTGGCA TGACACTTGA
    GTGGTTGGTT CCATACATCC ATATGCAGAT 60
CTTACATTCA CGTGAATATT GCAATGTCCA
    CTACAGACCA CATATAATAC AGAAATATCT 120
GTAGAACATT ATGCACAGAT ATGCACGATG GACT 154
(SEQ ID NO:3);

AGGATCACAG TTTGTGAAAG GATTTGGTGG
    AATTGGAGGT ATCTTGCGGT ACGAGTAGAT 60
TCAGGAATGG AATACCAAGG AGGAGATGAC
    GATTTTTGAC CTTGATGACT ACTAGGTAGT 120
CGACATGGTC CGCAAACGGC TCTCAGCATC
              ACCAGGAGCA T 161
(SEQ ID NO:4);

TTTTTTAACG GTTCCAACAT TTCACCACAT
    ATATTTCTGT GCAGTCTAGC CGAGAACGCC 60
ATGTAAATGG GTCACTGCGA GGCAGCGAAC
    GCAGCAATTT AGTTACTCTC GATCAAGGGA 120
GAAACAACAG TATGAC 136
(SEQ ID NO:5);

CCGTCTGCCA TGCCTCGGAA AATTGAGGAA
    TCAAGGACTT TCTACTCACA GCGCCGGCGG 60
AAGGATGCAA ATCTGTCAAG ATCAGAAAAA
    CAGGATAATG TAGTTCAAGG GTCGTGTAGC 120
AGGTAC 126
(SEQ ID NO:6);

TGTTTTGATT TCATCATGCT GTTTAATCTA
    GCATGTGCTT AGAAGGCTTG TTGGGCAGAG 60
TACAATATCT CCAGCAGTTC TAGAGACCAT
              TCACCACTGC GA 102
(SEQ ID NO:7);

CACAGTCAGC TCTTTATTGG ACATGTTAAC
    AAAAGCAGTT TAGTCAAAAA GACCAAAGCC 60
CATGTCATCC TCGGATTCTT CAGATTCTTC
    CTTCTTTGCT TCTACTTCTT CTCCTCAGCT 120
GGGGCAGCGG CGGCAGATGG AGCAGGACAC AGCAGG 156
(SEQ ID NO:8);

GGCCGCAACT AAAATGGTTT TTAATGGGAA
    CCAGAGATAT GGTTACAATT ACGTAGTCTG 60
ACACACTCAC ACACACACAC ATACCGTTGC
    CACCCCCCAA AATATCCATG AGTCAGTCCT 120
GATGTAGGTA CAATACGGTA CCTGGTACGA G 151
(SEQ ID NO:9);

and

AGCCTGGCAA GATGGACTCA GGGTGAGCAC
    AGACAGGATC GCAGGGAGAG GCATATAGCT 60
GACTCTGAGT TCTGACAGCT CTCTGTACCA
    GTGTACCTGT ATTGTACTAC ATCGATG 157
(SEQ ID NO:10).

2. A probe for the diagnosis or prognosis of malignant disease, which comprises a sequence fully complementary to a polynucleotide sequence of claim 1.

* * * * *